United States Patent
Epstein et al.

(10) Patent No.: US 11,678,860 B2
(45) Date of Patent: Jun. 20, 2023

(54) SYSTEM FOR VISUALIZATION AND CONTROL OF SURGICAL DEVICES UTILIZING A GRAPHICAL USER INTERFACE

(71) Applicant: ACESSA HEALTH INC., Austin, TX (US)

(72) Inventors: Gordon E. Epstein, Austin, TX (US); Richard Spero, Austin, TX (US)

(73) Assignee: ACESSA HEALTH INC., Austin, TX (US)

( * ) Notice: Subject to any disclaimer, the term of this patent is extended or adjusted under 35 U.S.C. 154(b) by 232 days.

(21) Appl. No.: 17/098,315

(22) Filed: Nov. 13, 2020

(65) Prior Publication Data
US 2021/0059637 A1 Mar. 4, 2021

Related U.S. Application Data

(63) Continuation of application No. 14/537,899, filed on Nov. 10, 2014, now Pat. No. 10,835,203.
(Continued)

(51) Int. Cl.
*A61B 8/00* (2006.01)
*A61B 8/13* (2006.01)
(Continued)

(52) U.S. Cl.
CPC .................. *A61B 8/13* (2013.01); *A61B 8/12* (2013.01); *A61B 8/463* (2013.01); *A61B 34/20* (2016.02); *A61B 34/25* (2016.02); *A61B 5/743* (2013.01); *A61B 5/744* (2013.01); *A61B 5/7435* (2013.01); *A61B 2034/2063* (2016.02);
(Continued)

(58) Field of Classification Search
None
See application file for complete search history.

(56) References Cited

U.S. PATENT DOCUMENTS

| 6,241,725 B1 | 6/2001 | Cosman |
| 2003/0074011 A1* | 4/2003 | Gilboa ..................... A61B 5/06 606/130 |

(Continued)

OTHER PUBLICATIONS

Begamini, MD. et al., Laparoscopic radiofrequency thermal ablation: A new approach to symptomatic uterine myomas, American Journal of Obstetrics and Gynecology, 192:768-73, Varese, Italy, Mar. 2005.
(Continued)

*Primary Examiner* — Joel F Brutus
(74) *Attorney, Agent, or Firm* — Vista IP Law Group, LLP

(57) ABSTRACT

A system for visualizing and guiding a surgical device having a first imaging device of a first type and has a first image output. The first imaging device is positioned to image an area being subject to surgery. A second imaging device of a second type has a second image output. The second imaging device is positioned to image an area being subject to surgery. A computer is coupled to receive the first and second image outputs and a computer software program, resident in the computer receives and displays information received from the surgical device and/or for guiding the operation of the surgical device and for generating a graphic user interface including selectable menu and submenu items. The surgical device is coupled to the computer.

20 Claims, 17 Drawing Sheets

Related U.S. Application Data

(60) Provisional application No. 61/902,382, filed on Nov. 11, 2013.

(51) Int. Cl.
    *A61B 8/12*     (2006.01)
    *A61B 34/20*     (2016.01)
    *A61B 34/00*     (2016.01)
    A61B 5/00     (2006.01)
    A61B 90/00     (2016.01)

(52) U.S. Cl.
    CPC ... *A61B 2090/364* (2016.02); *A61B 2090/371* (2016.02); *A61B 2090/378* (2016.02)

(56) References Cited

U.S. PATENT DOCUMENTS

| | | |
|---|---|---|
| 2007/0225553 A1 | 9/2007 | Shahid |
| 2009/0204911 A1 | 8/2009 | Sekiguchi |
| 2010/0312103 A1 | 12/2010 | Gorek et al. |
| 2011/0046483 A1* | 2/2011 | Fuchs ................ A61B 8/4245 606/20 |
| 2013/0197357 A1 | 8/2013 | Green |
| 2014/0343404 A1 | 11/2014 | Razzaque et al. |

OTHER PUBLICATIONS

Non-Final Office Action for U.S. Appl. No. 17/135,203 dated Jan. 26, 2023.

* cited by examiner

SYSTEM FOR VISUALIZATION AND CONTROL OF SURGICAL DEVICES UTILIZING A GRAPHICAL USER INTERFACE

RELATED APPLICATION DATA

This application is a continuation of U.S. patent application Ser. No. 14/537,899 filed Nov. 10, 2014, now U.S. Pat. No. 10,835,203, which claims priority to U.S. Provisional Application Ser. No. 61/902,382, filed Nov. 11, 2013, both of which are hereby incorporated herein by reference in their entirety.

FIELD OF THE INVENTION

The invention relates to a system for the control and visualization of medical devices positioned in a patient's body for ablation of a tumor, such as a uterine fibroid and, more particularly, to a user interface for visualizing an ultrasound image and dynamic 3D avatar guidance of an ablation probe during a surgical procedure, enabling the operator to make operational decisions based on those visualizations.

BACKGROUND OF THE INVENTION

Advances in technology have resulted in graphical user interfaces that allow a practitioner or other medical professional to visualize a plurality of images obtained from multiple medical devices such as a laparoscopic cameras and ultrasound probes together on one screen. Current systems use simple picture in picture technology to view smaller laparoscopic camera images and ultrasound images on a larger guidance system screen.

DETAILED DESCRIPTION OF THE INVENTION

Figure 1:
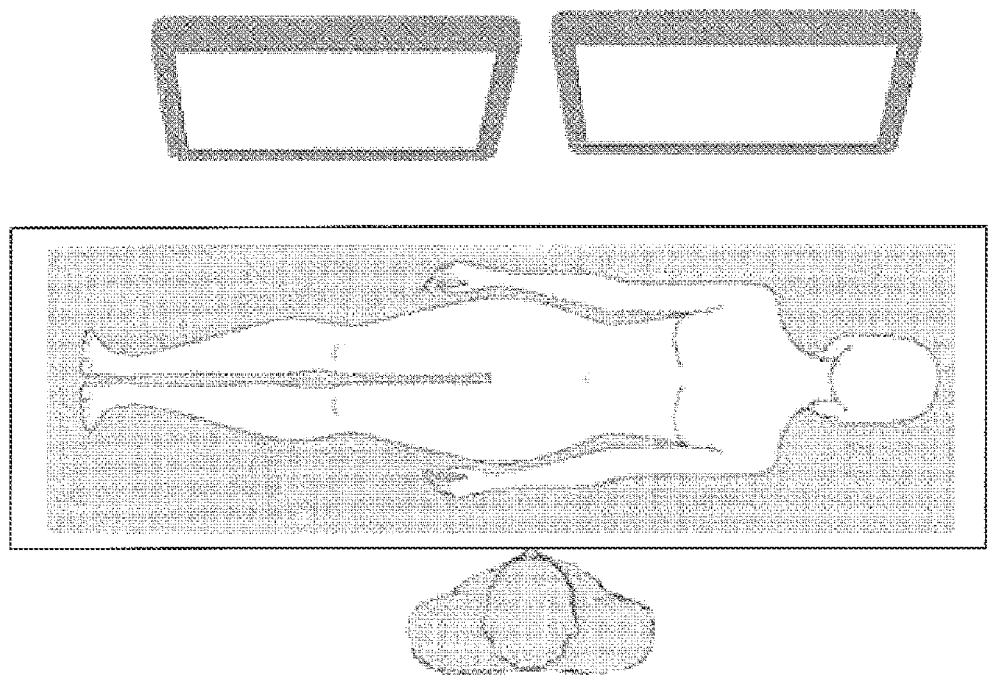
FIG. 1 illustrates an overview of the operating room layout useful with the inventive system.

FIG. 1 illustrates an overview of the typical operating room layout for the present invention. The surgeon 10 is standing on the left hand side of patient 12 who is lying on operating table 14. Surgeon 10 may also stand on the right hand of patient 12, whichever is most convenient. Two screens 16, 18 are located on the opposite side of patient 12 from surgeon 10. Screen 16 displays video from a laparoscopic camera and screen 18 displays the inventive user interface. Screens 16 and 18 can be any type of display monitor such as a computer monitor, television, handheld device screen, etc.

Figure 2:
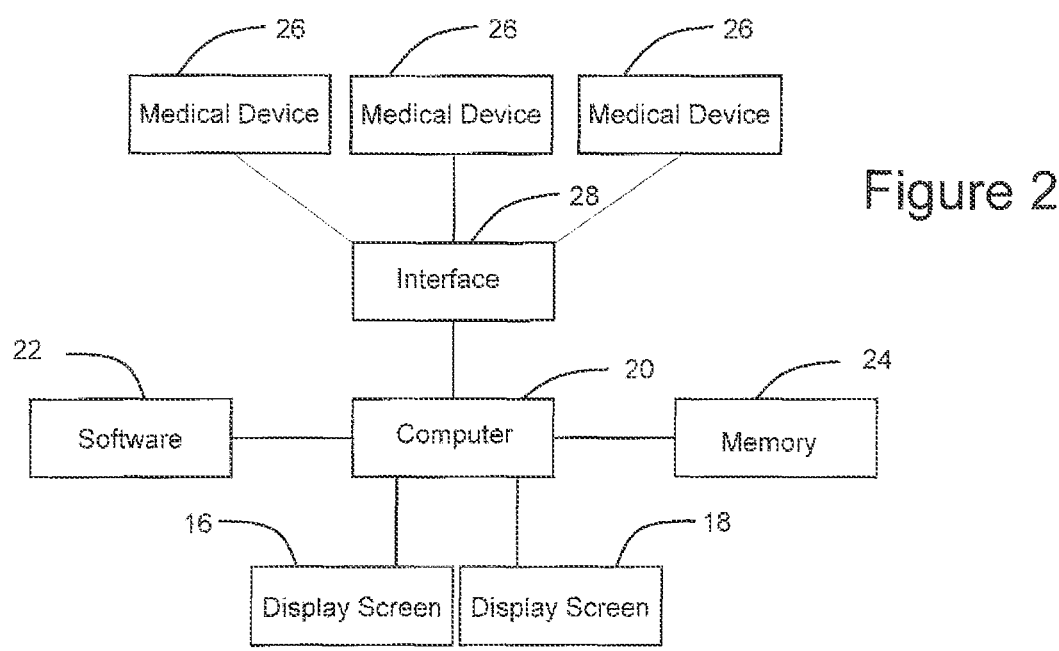
FIG. 2 illustrates an ablation system incorporating computer controls in accordance with the inventive system.

FIG. 2 illustrates an exemplary system for implementing the present invention. Computer 20 may be any control device, such as a microprocessor, personal computer, or a more powerful or less powerful computer with typical computer-type operating system. Computer 20 includes display screens 16 and 18, which may optionally be a touchscreen to provide a second means of navigation.

Personal computer 20 also incorporates software 22. Software 22 may be of any type for use on any suitable computing device, and which may be easily written by a programmer of ordinary skill in the art who is informed by this specification. The software is responsive to produce images illustrated in the drawings and stored in memory 24 of computer 20. The software performs navigation functions by being responsive to touchscreen entry on display screen 18. Likewise, in response to operation by touching display screen 18, computer 20 may cause the screen to change in one of the ways described in full detail below.

Computer 20 communicates with a plurality of medical devices 26 through an interface board 28. Medical devices 26 include an ablation instrument, laparoscopic camera, and ultrasound probe, or any other instrument useful in imaging and treating uterine fibroids or other pelvic tumors. At the same time, medical devices 26 provide information to interface 28 which in turn provides this information to personal computer 20 for display on display screens 16 and 18.

Figure 3:
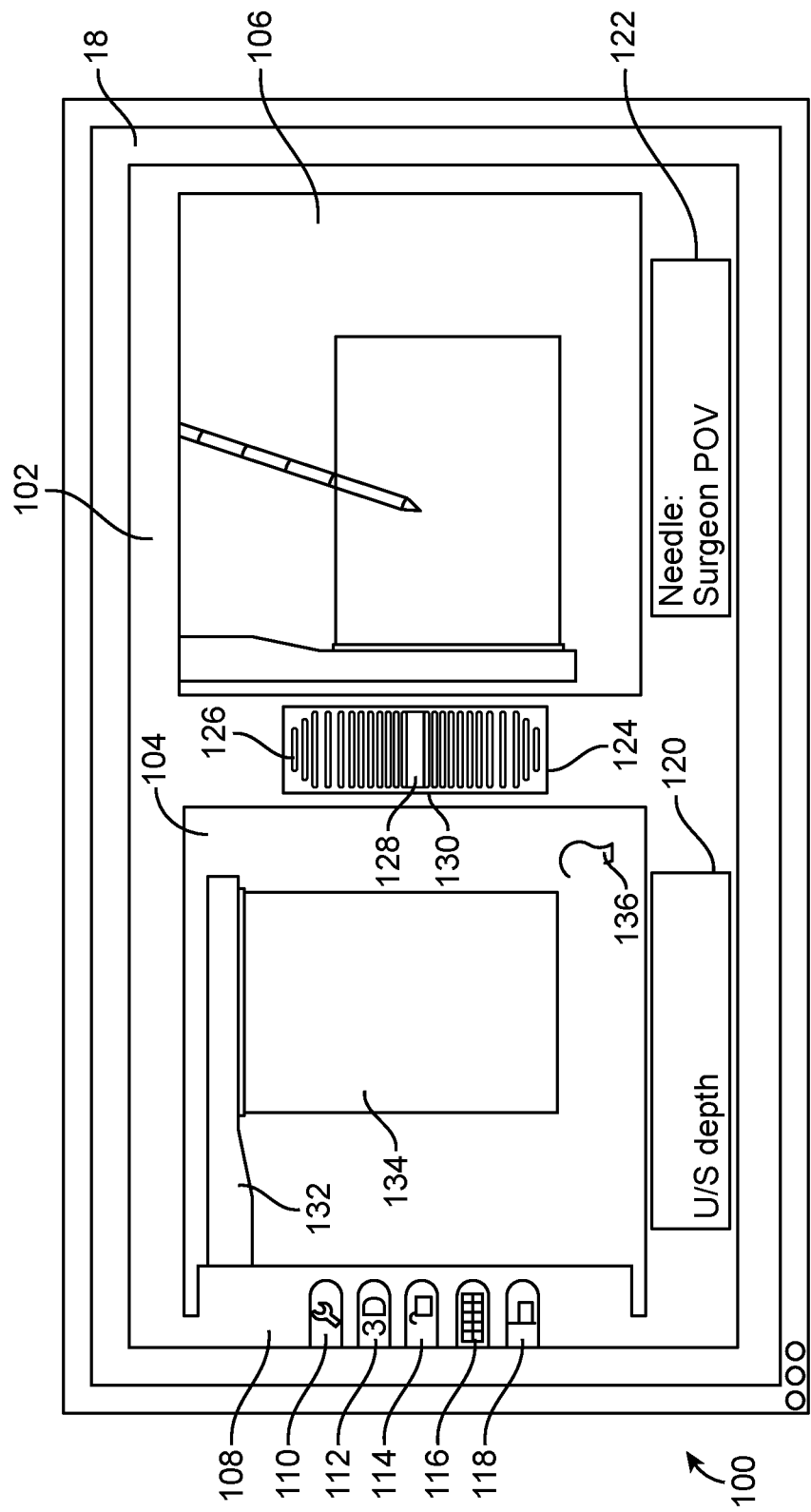
FIG. 3 shows the inventive graphical user interface screen in which the display is divided into two separate screens with an associated text box and a control tab.

FIG. 3 illustrates the preferred embodiment of the inventive user interface. Software takes data from transducers located on an ablation probe, and data from transducers on an ultrasound probe and displays it to a user via user interface 100 on display screens 18. Screen 18 displays the inventive user interface 100. Video from a laparoscopic camera is communicated directly to display screen 16. User interface has an overlay 102 that provides the appearance of a physical bezel that divides the display into two screens 104, 106. Overlay 102 has a control tab 108 located on the left hand side of overlay 102. Control tab 108 has five selections to choose from 110, 112, 114, 116, 118.

Overlay 102 includes two text boxes 120, 122. Text box 120 is located under screen 104 and displays information relating to what is displayed on screen 104. For example, text box 120 may display the depth of the ultrasound.

Text box 122 is located under screen 106 and displays information relating to what is displayed on screen 106. For example, text box 122 may display the point of view of the image displayed on screen 106.

Overlay 102 has a meter 124 located in between screens 104, 106. Meter 124 indicates the distance between the tip of an ablation probe to the plane of an ultrasound scan. Meter 124 has hash marks 126 to indicate the distance from the tip of the ablation probe to the plane of the ultrasound scan. The central hash mark 128 is green and indicates that the tip of the ablation probe is in line with the plane of the ultrasound scan. The hash marks above central hash mark 128 are blue and indicate that the ablation needle is behind the plane of the ultrasound scan. The space between the hash marks increases the further away from central hash mark 128 you get. The hash marks below central hash mark 128 are yellow and indicate that the ablation needle is in front of the plane of the ultrasound scan. Meter 124 also has a sliding hash mark 130 that slides up and down meter 124 indicating the dynamic location of the tip of the ablation needle relative to the plane of the ultrasound scan. Sliding hash mark 130 is translucent, allowing the user to see the blue, yellow, or green hash mark underneath.

Screen 104 is used to display a virtually complete ultrasound screen in two dimensions. Screen 104 contains a photorealistic avatar of ultrasound shaft 132. Ultrasound shaft 132 is placed above the display of ultrasound beam 134 in order to provide orientation for ultrasound beam 134 to the user. This enables the user to easily see the direction the ablation probe is entering the ultrasound beam.

Screen 106 also displays icon 136, which indicates the direction the ultrasound beam is pointing in relation to the uterus of patient 12.

Icon 136 may be a depiction of a right hand with the letter "R" to indicate that ultrasound beam 134 is pointing towards the right hand of patient 12.

Icon 136 may be a depiction of a left hand with the letter "L" to indicate that ultrasound beam 134 is pointing towards the left hand of patient 12.

Icon 136 may be a depiction a person's head to indicate that ultrasound beam 134 is pointing towards the head of patient 12.

Icon 136 may also be a depiction of feet to indicate that ultrasound beam 134 is pointing towards the feet of patient 12.

Icon 136 will change in real time between these depictions depending on the direction ultrasound beam 134 is pointing. For instance, if a user moves an ultrasound beam from pointing towards the feet of a patient towards to the right hand of the patient, icon 136 will change from a depiction of feet to a depiction of a right hand with the letter R. This is done automatically without any input from the surgeon. The surgeon also has the capability to freeze the orientation view if desired.

Figure 4:
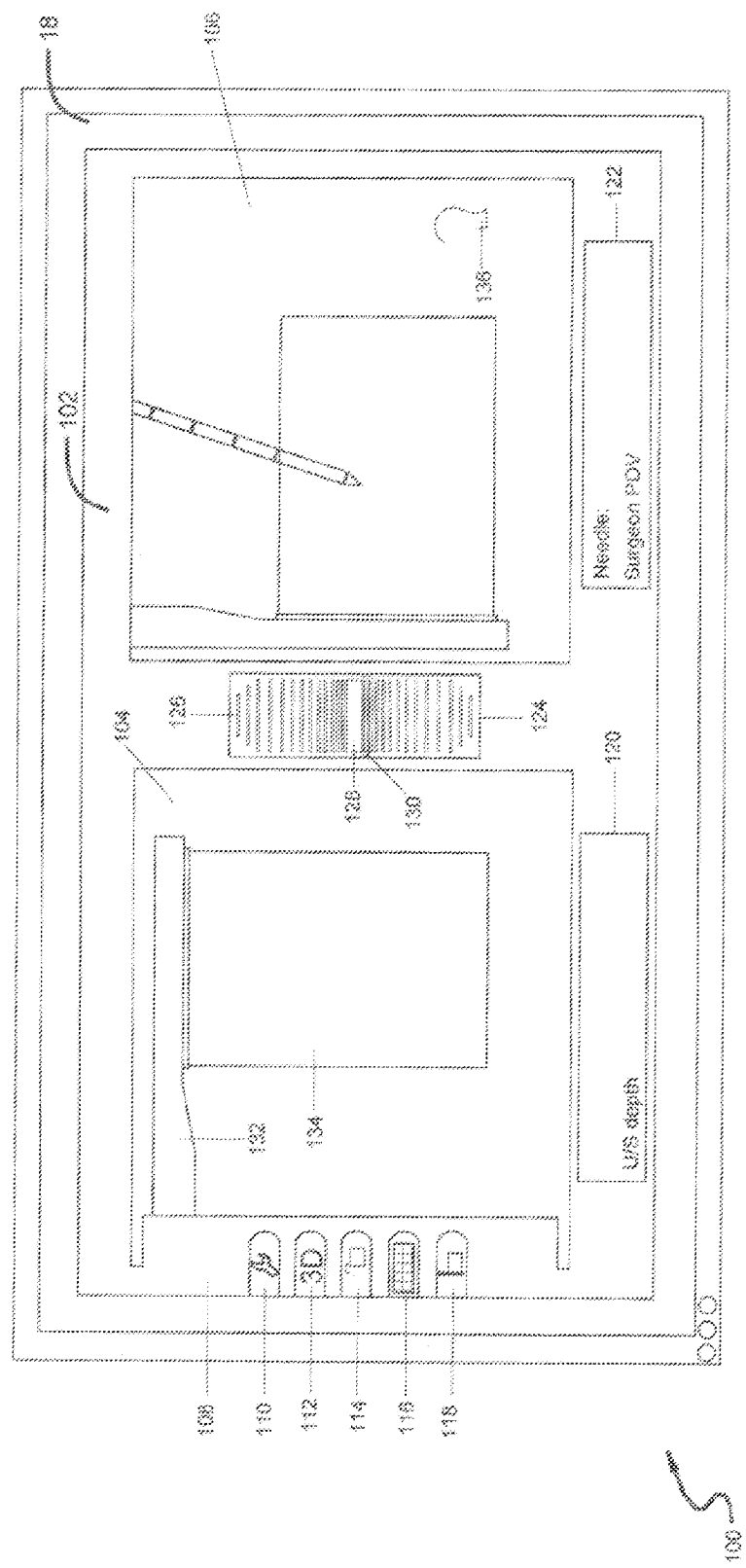
FIG. 4 illustrates the inventive user interface being displayed from the surgeon's point of view with the ultrasound beam facing the patient's head.

FIG. 4 illustrates the inventive user interface with the ultrasound beam facing the patient's head in the surgeon's point of view. Icon 136 displays as a depiction of a human face in profile.

Figure 5:
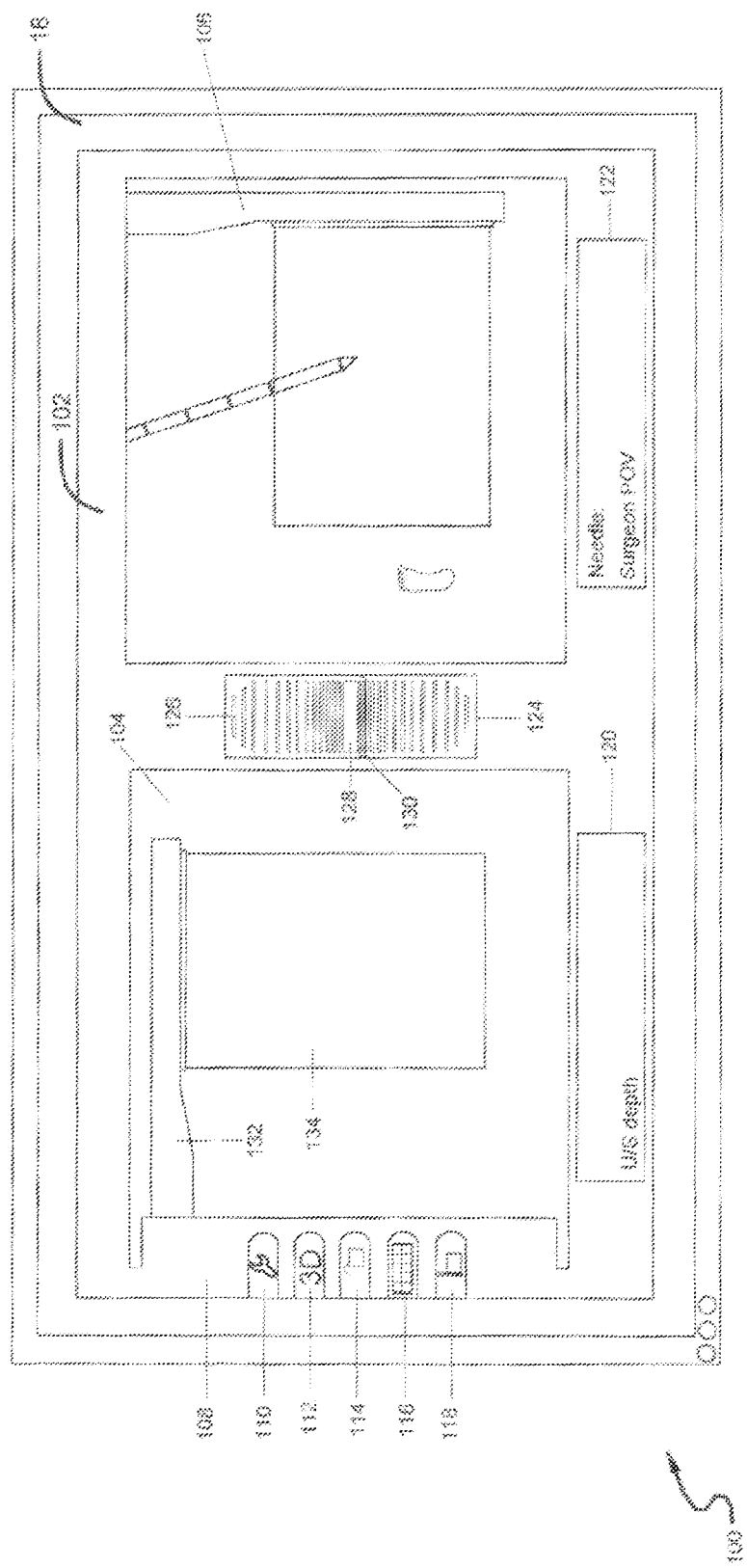
FIG. 5 illustrates the inventive user interface being displayed from the surgeon's point of view with the ultrasound beam facing the patient's feet.

FIG. 5 illustrates the inventive user interface with the ultrasound beam facing the patient's feet in the surgeon's point of view. Icon 136 displays as depiction of a human foot.

Figure 6:
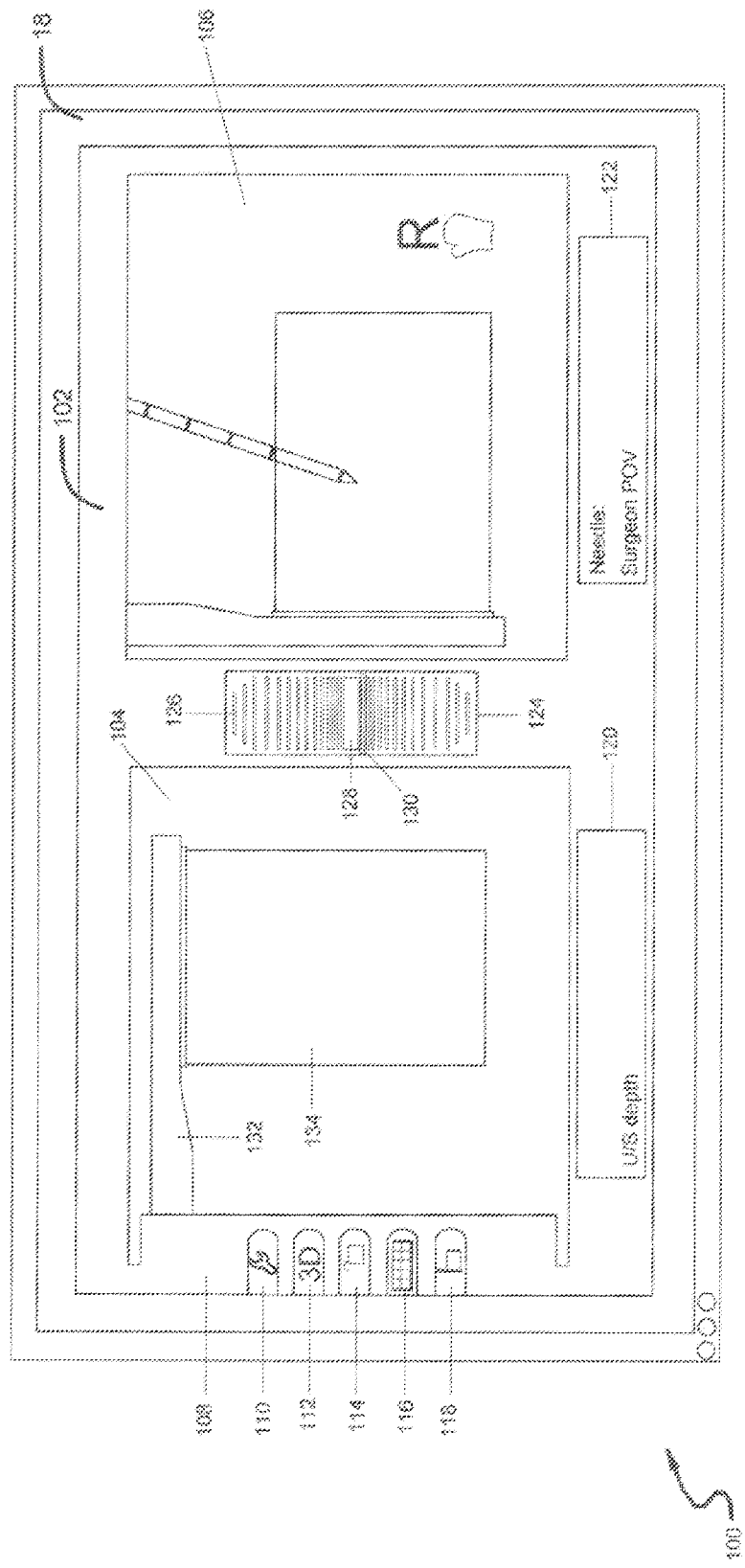
FIG. 6 illustrates the inventive user interface being displayed from the laparoscopic point of view with the ultrasound beam facing the patient's right hand.

FIG. 6 illustrates the inventive user interface with the ultrasound beam facing the patient's right hand in the laparoscopic point of view. Icon 136 displays as a depiction of a right human hand with the letter "R." The letter "R" can be displayed inside the depiction of the human hand or alternatively, in the immediate surrounding area of Icon 136, such as to the right, to the left, on top of, or beneath, Icon 136.

Figure 7:
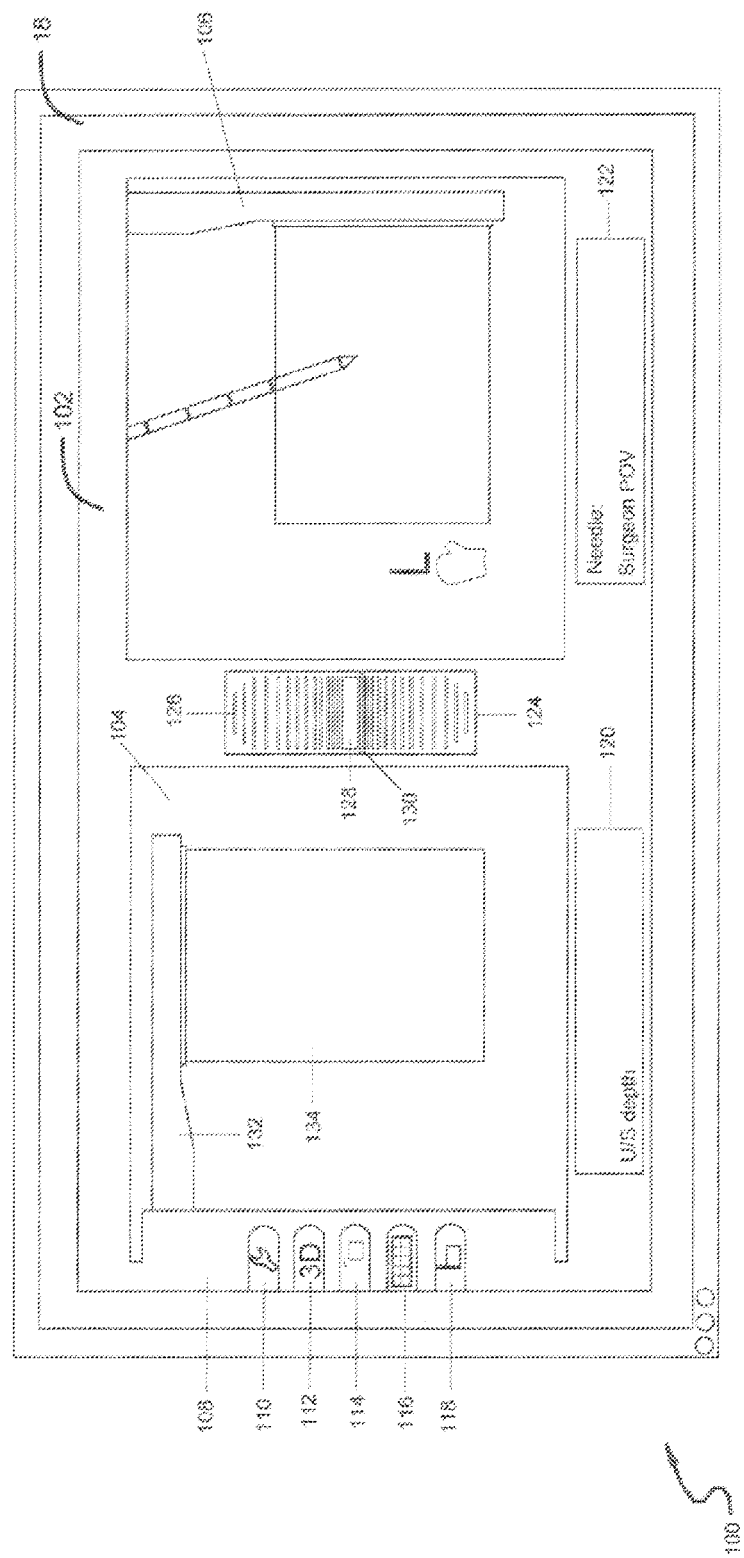
FIG. 7 illustrates the inventive user interface being displayed from the laparoscopic point of view with the ultrasound beam facing the patient's left hand.

FIG. 7 illustrates the inventive user interface with the ultrasound beam facing the patient's left hand in the laparoscopic point of view. Icon 136 displays as a depiction of a left human hand with the letter "L." The letter "L" can be displayed inside the depiction of the human hand or alternatively, in the immediate surrounding area of Icon 136, such as to the right, to the left, on top of, or beneath, Icon 136.

The display of ultrasound beam 134 will also rotate direction depending upon the orientation of ultrasound beam 134. For example, in FIG. 4, ultrasound beam 134 is pointed at the patient's head, thus icon 136 will be a depiction of a head ultrasound beam 134 will point to the right. When the ultrasound transducer is physically rotated so that it points to the patient's right hand, the transducer shaft 132 will occlude the image of ultrasound beam 134. In order to provide a user with a view of the system, the system will virtually rotate ultrasound beam 134 back to the right and icon 136 will display a right hand, to signify that ultrasound beam 134 is pointing to the patient's right hand, as seen in FIG. 6. This happens whenever ultrasound shaft 132 is physically rotated 90 degrees as shown in FIG. 8.

Figure 8:
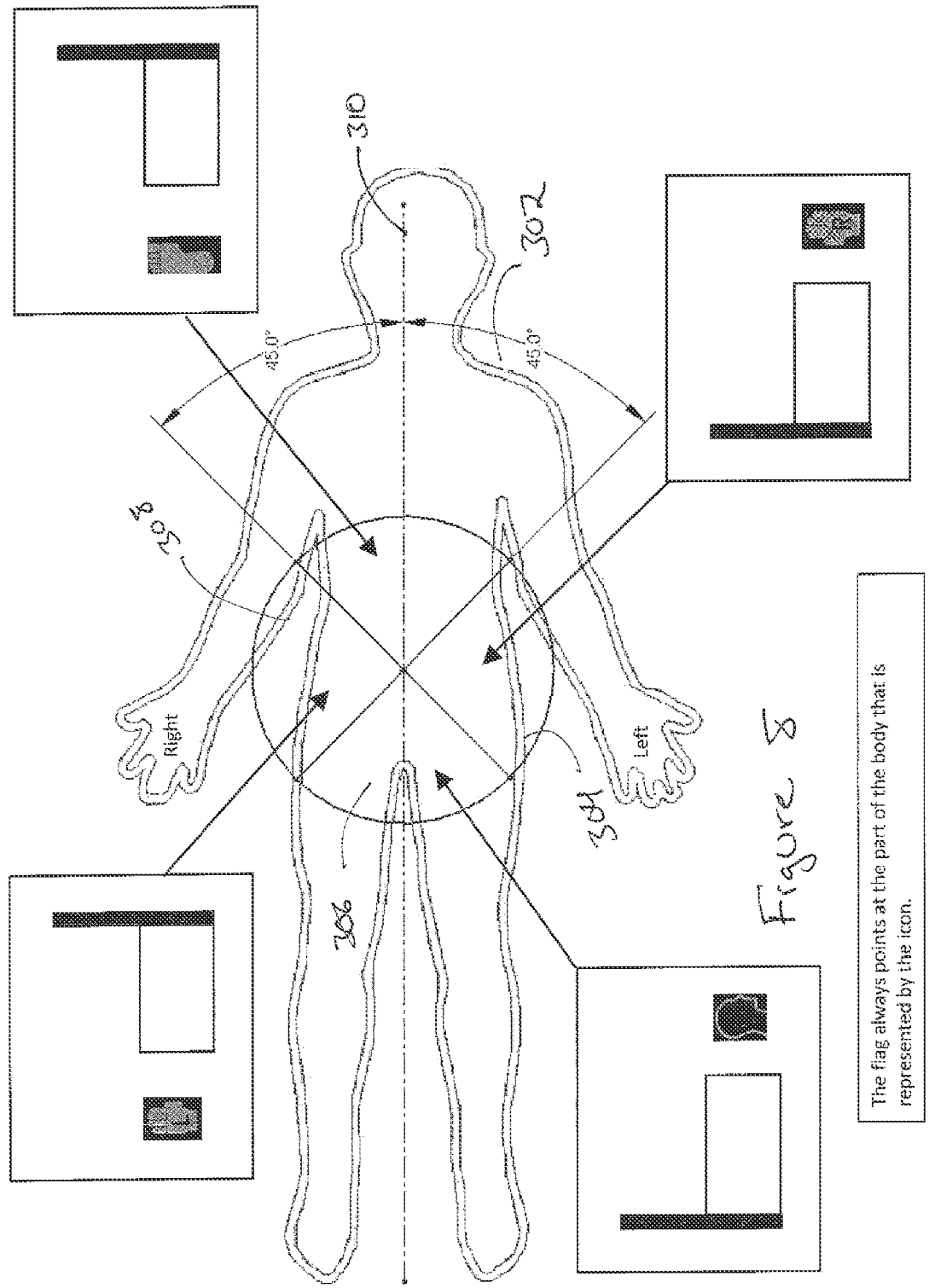
FIG. 8 shows an overhead view of a patient's body divided into four quadrants and the icon depictions associated with each quadrant.

FIG. 8 illustrates which graphical depiction Icon 136 will display when the ultrasound probe is in four defined quadrants of patient 12. The depiction is based on the location of the ultrasound probe in patient 12 in relation to the uterus of patient 12. Patient 12 is divided by a centerline 310 y-axis with the patient's head being 0 degrees and the patient's feet being 180 degrees. Patient is then divided by an x-axis through the uterus. Patient 12 is then further divided into four 90 degree quadrants 302, 304, 306, and 308.

Quadrant 302 is defined between 315 degrees to 45 degrees measured from the uterus. When the ultrasound probe is in quadrant 302, Icon 136 will display a depiction of a human foot since to view the uterus the ultrasound beam would have to be directed towards the patient's feet.

Quadrant 304 is defined between 45 degrees and 135 degrees. When the ultrasound probe is in quadrant 304, Icon 136 will display a depiction of a right human hand with the letter "R".

Quadrant 306 is defined between 135 degrees and 225 degrees. When the ultrasound probe is in quadrant 306, Icon 136 will display a depiction of a human face in profile.

Quadrant 308 is defined between 225 degrees and 315 degrees. When the ultrasound probe is in quadrant 308, Icon 136 will display a depiction of a left human hand with the letter "L".

Referring back to FIG. 3, screen 106 is used to display ablation probe guidance information in either two dimensions or three dimensions.

Again referring to FIG. 3, overlay 102 has a control tab 108 containing controls 110, 112, 114, 116, and 118 located on the left side of overlay 102 which can be used by a surgeon or medical professional while maintaining the sterile field.

Control 110 has a depiction of a tool, and when selected allows a medical professional to change the display of the system.

Control 112 displays "3D," and when selected allows a medical professional to view the guidance information on screen 106 in three dimension.

Control 114 has a depiction of a lock, and when selected allows a medical professional to freeze the point of view being displayed.

Control 116 has a depiction of a grid, and when selected displays a grid over the ultrasound data, which decreases the need for measurement of the dimensions of any tumors or masses being imaged.

Control 118 has a depiction of an ultrasound probe, and when selected brings screen 104 into full-screen, eliminating screen 106.

Figure 9:
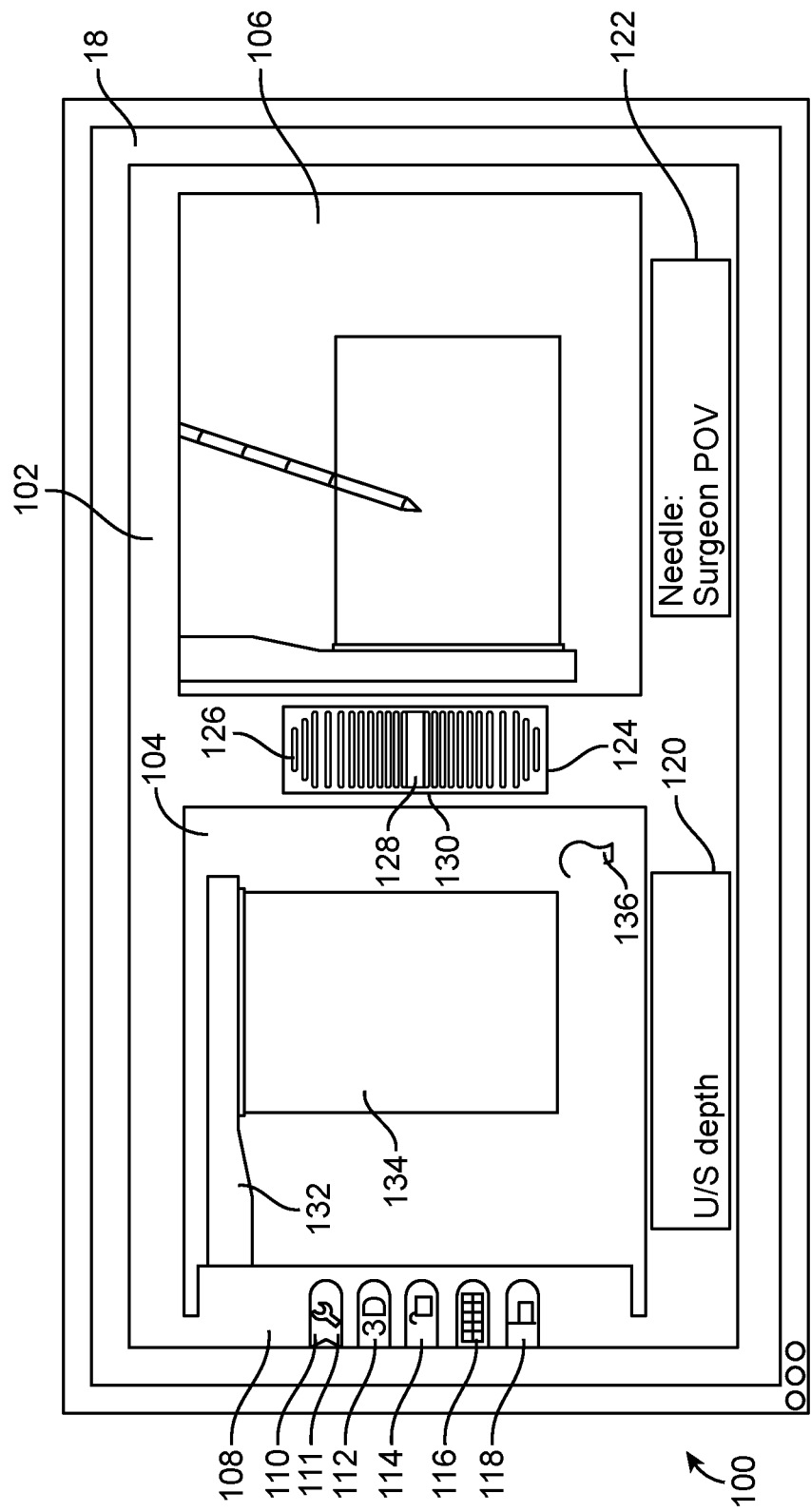
FIG. 9 shows the graphical user interface screen in which the navigational tool has scrolled to the tool icon control button.
Figure 10:
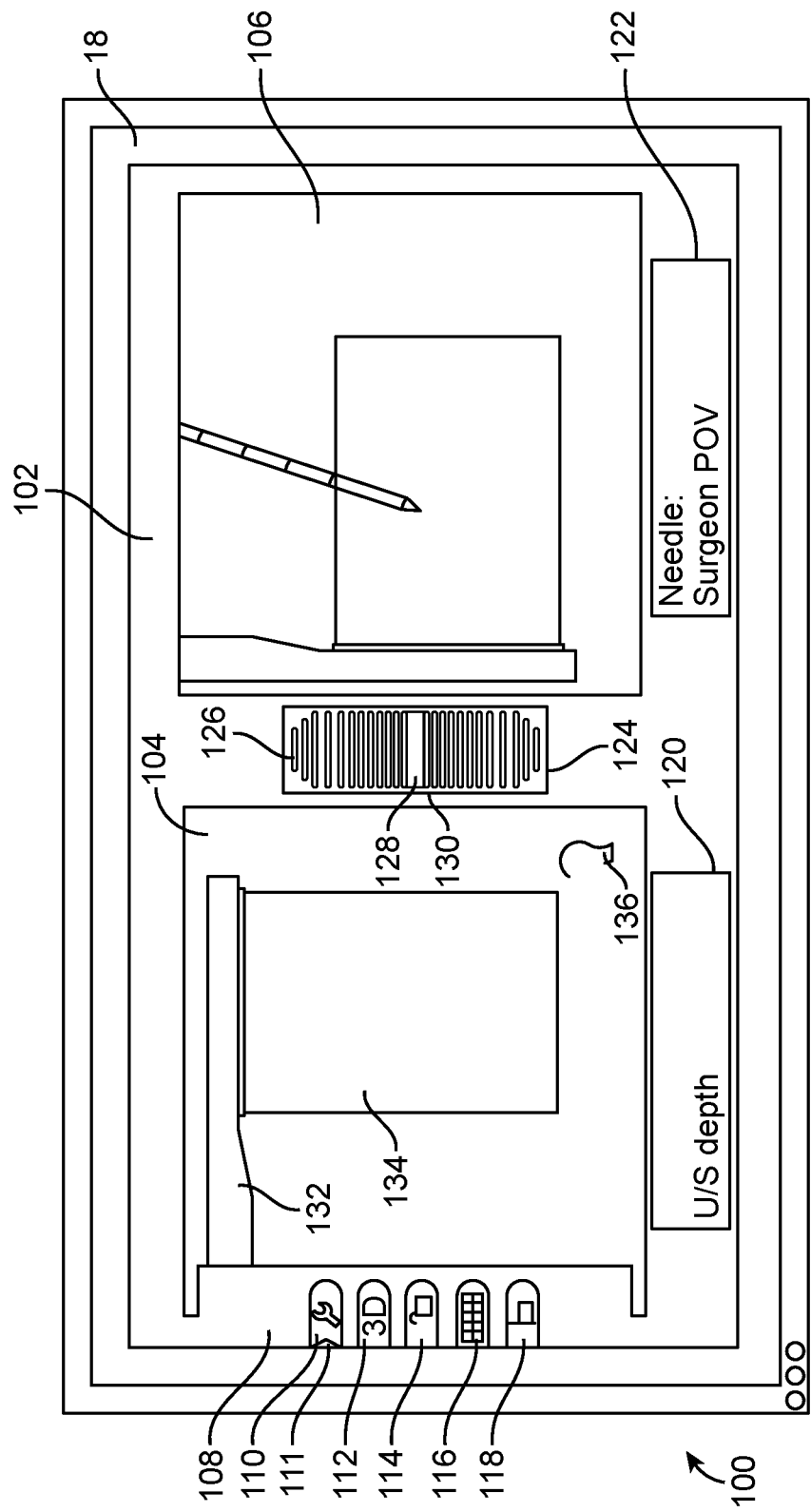
FIG. 10 shows the graphical user interface in which the tool icon control button has been selected.

Selecting control 110 (FIG. 9) with navigational tool 111 causes the system to exit the display of FIG. 2 and go to the display of FIG. 10.

Figure 11:
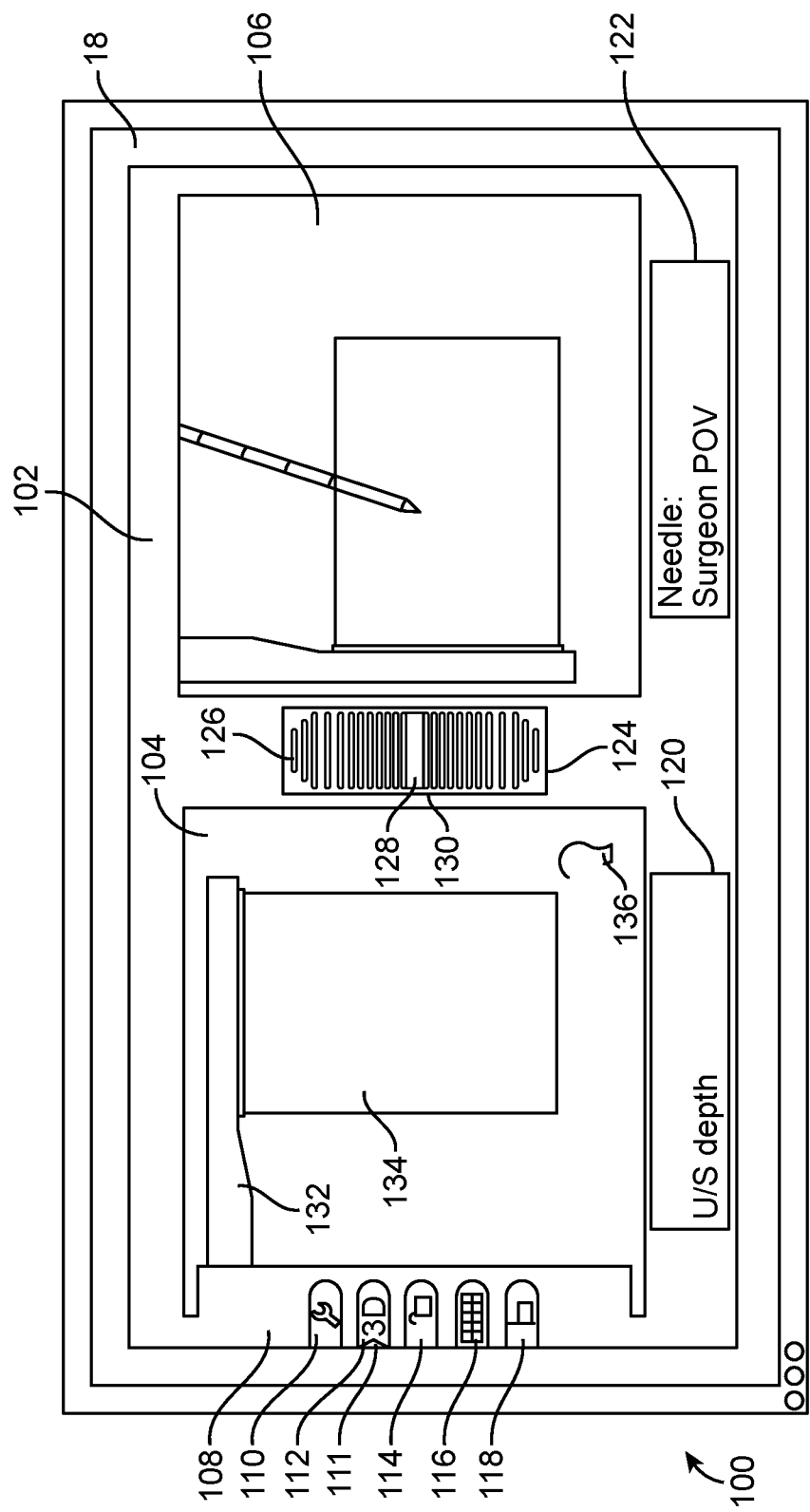
FIG. 11 shows the graphical user interface screen in which the navigational tool has scrolled to the three dimension icon control button.
Figure 12:
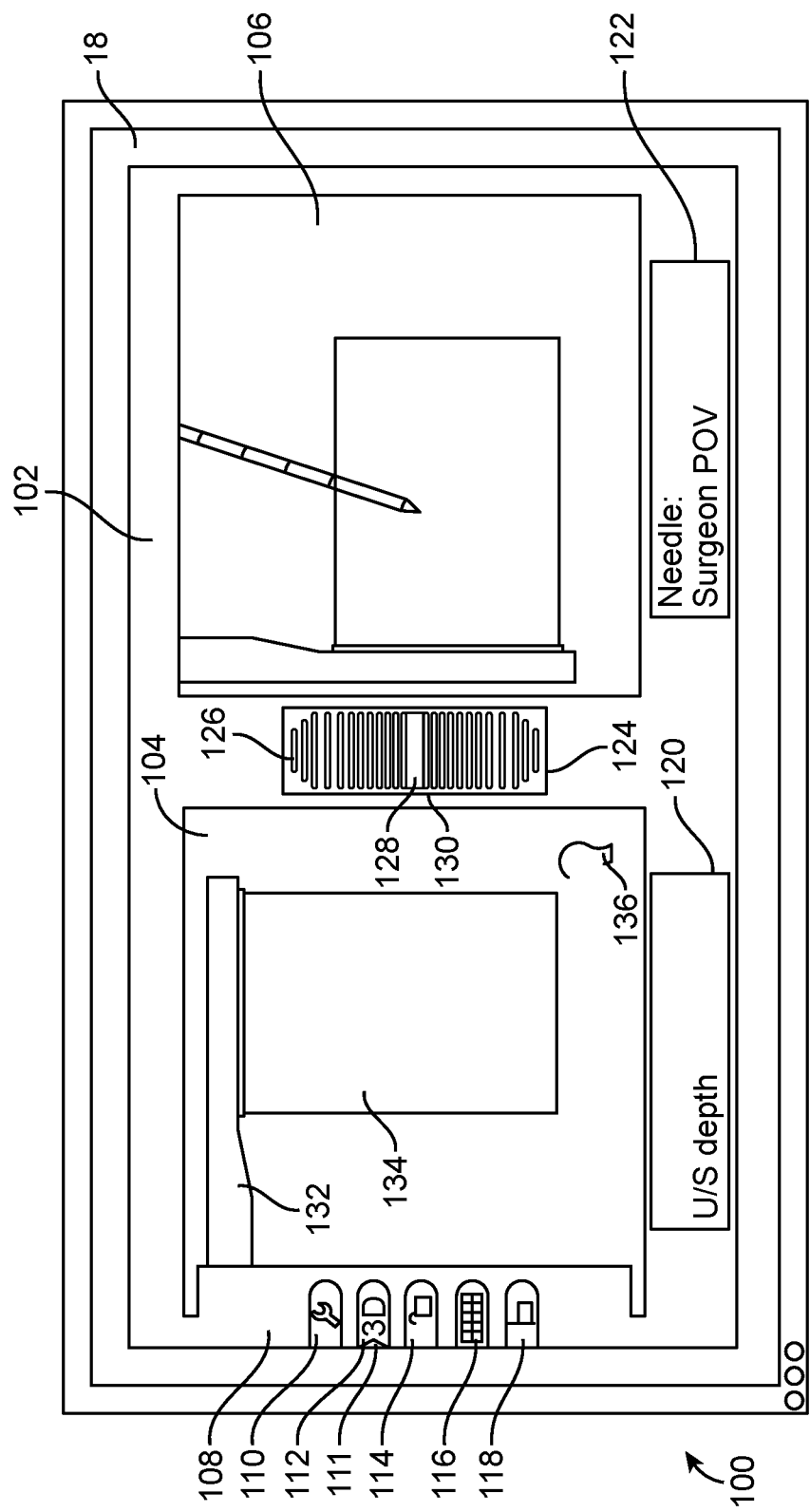
FIG. 12 shows the graphical user interface screen in which the navigational screen is displayed in three dimension.

Selecting control 112 (FIG. 11) with navigational tool 111 causes the system to exit the display of FIG. 2 and go to the display of FIG. 12. The display of FIG. 12 is substantially the same as the display of FIG. 2, except that screen 106 is now viewed as three-dimensional as opposed to two-dimensional.

Figure 13:
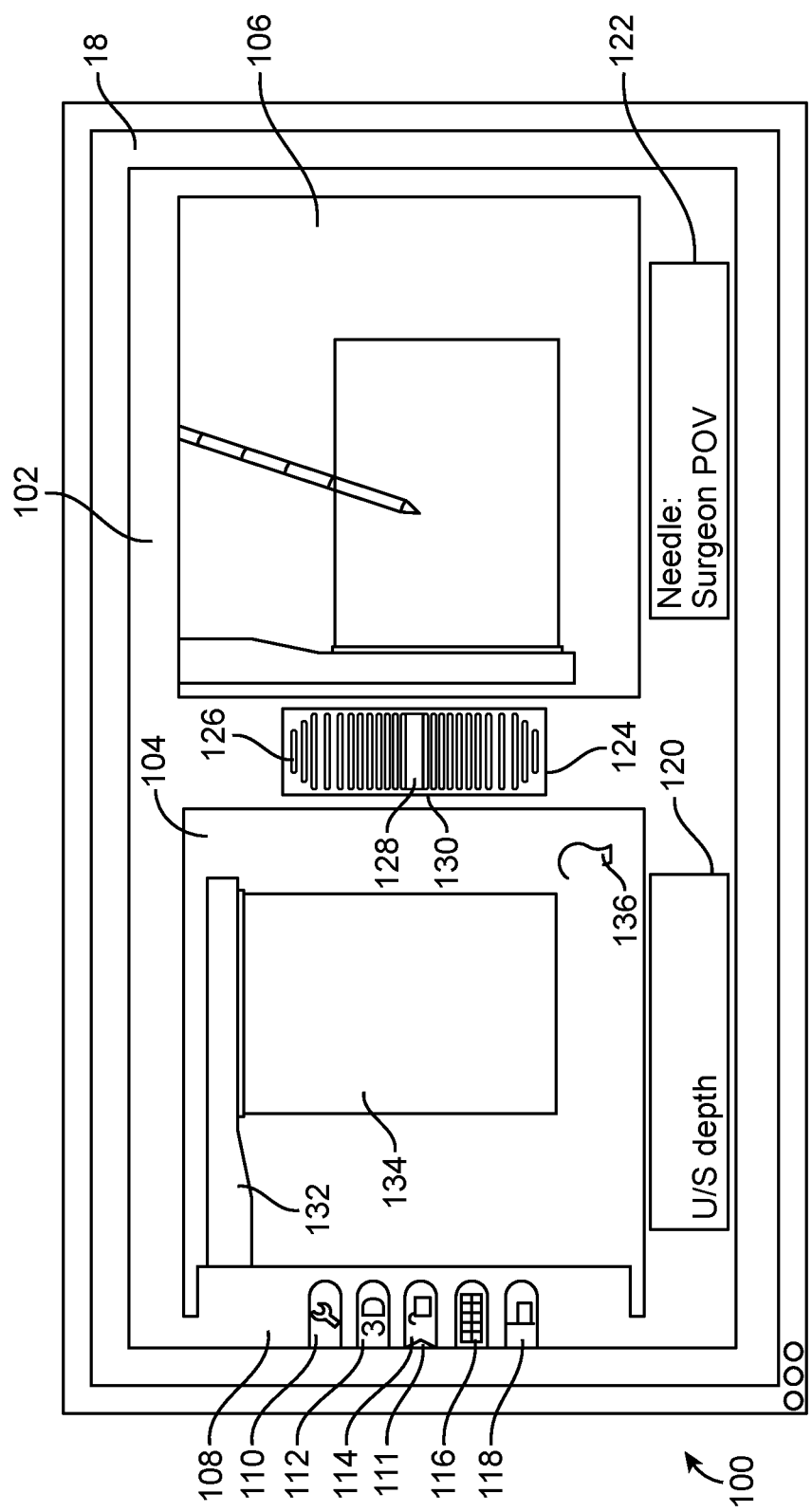
FIG. 13 shows the graphical user interface in which the navigational tool has scrolled to the control button.

Selecting control 114 (FIG. 13) with navigational tool 111 causes the display in FIG. 2 to become locked in the currently displayed point of view. Thus, the display in screen 104 will not automatically switch point of views based on the placement of the ultrasound probe. Instead, the screen will stay locked in the point of view at the time of selection of control 114.

Figure 14:
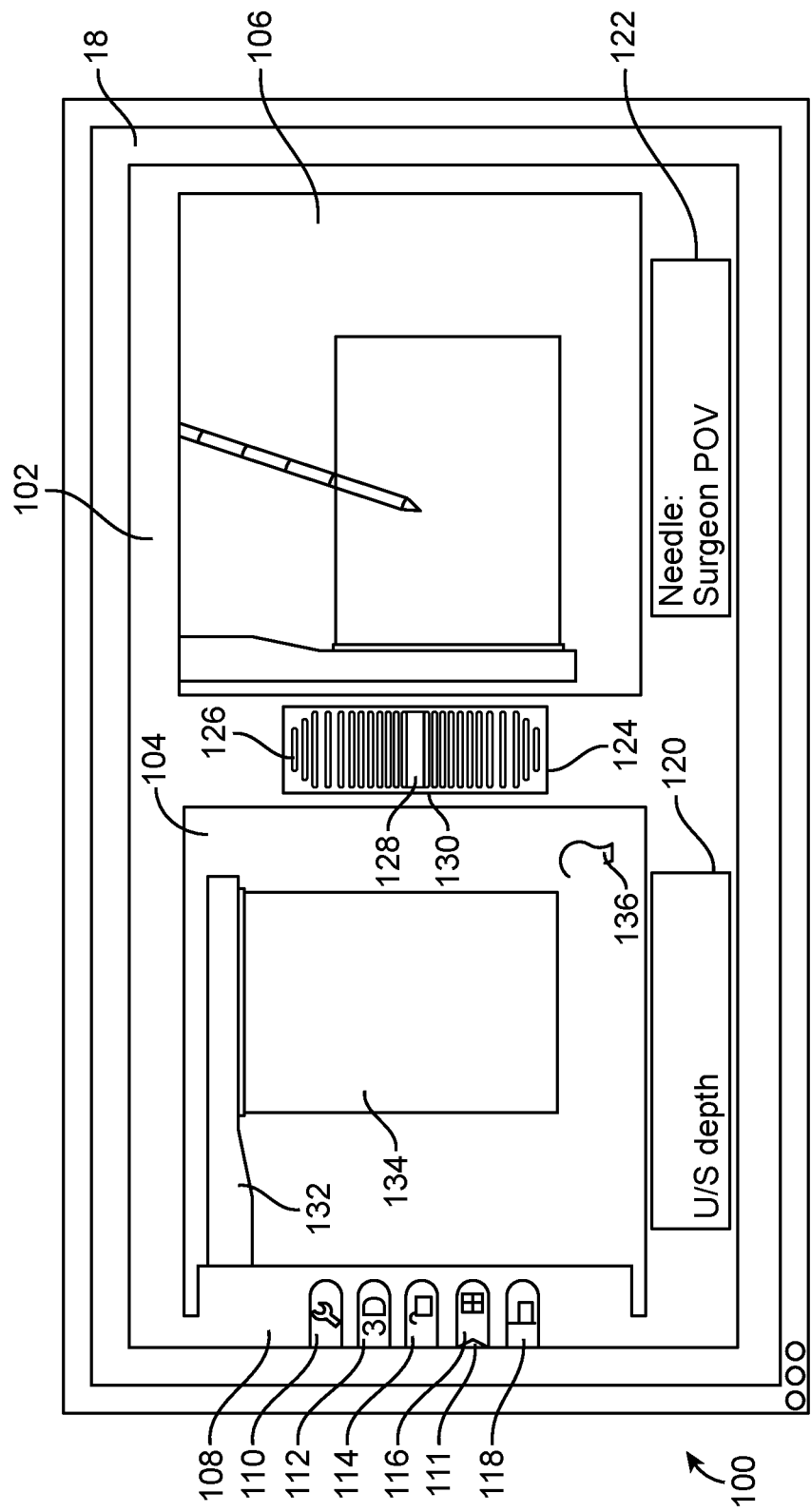
FIG. 14 shows the graphical user interface in which the navigational tool has scrolled to the grid icon control button.
Figure 15:
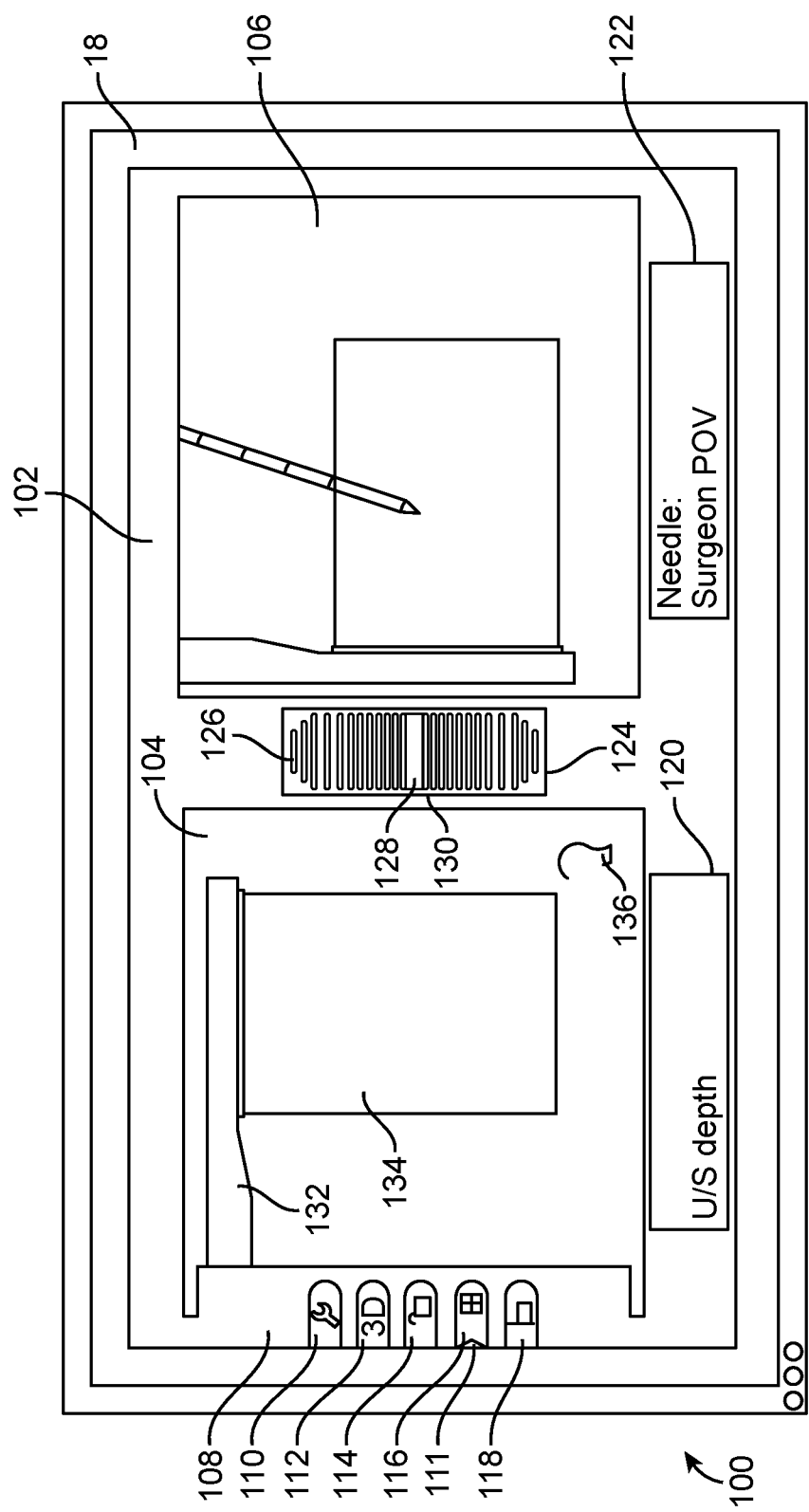
FIG. 15 shows the graphical user interface in which a grid is displayed on the GUI.

Selecting control 116 (FIG. 14) with navigational tool 111 causes grid 138 to be displayed over screen 104 as illustrated in FIG. 15. Grid 138 decreases the need for measurement of the dimensions of any tumors or masses being imaged.

Figure 16:
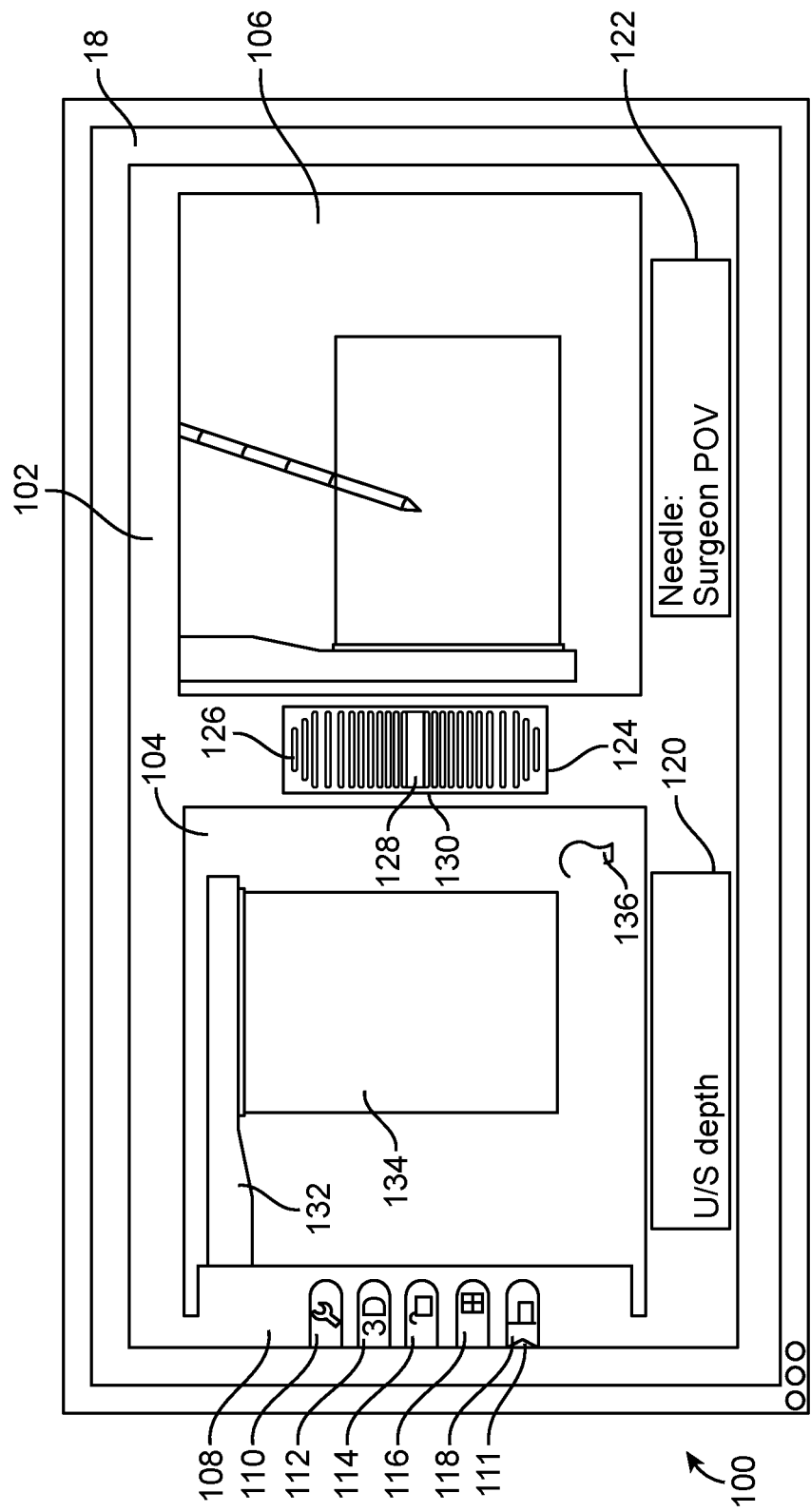
FIG. 16 shows the graphical user interface in which the navigational tool has scrolled to ultrasound probe icon control button.
Figure 17:
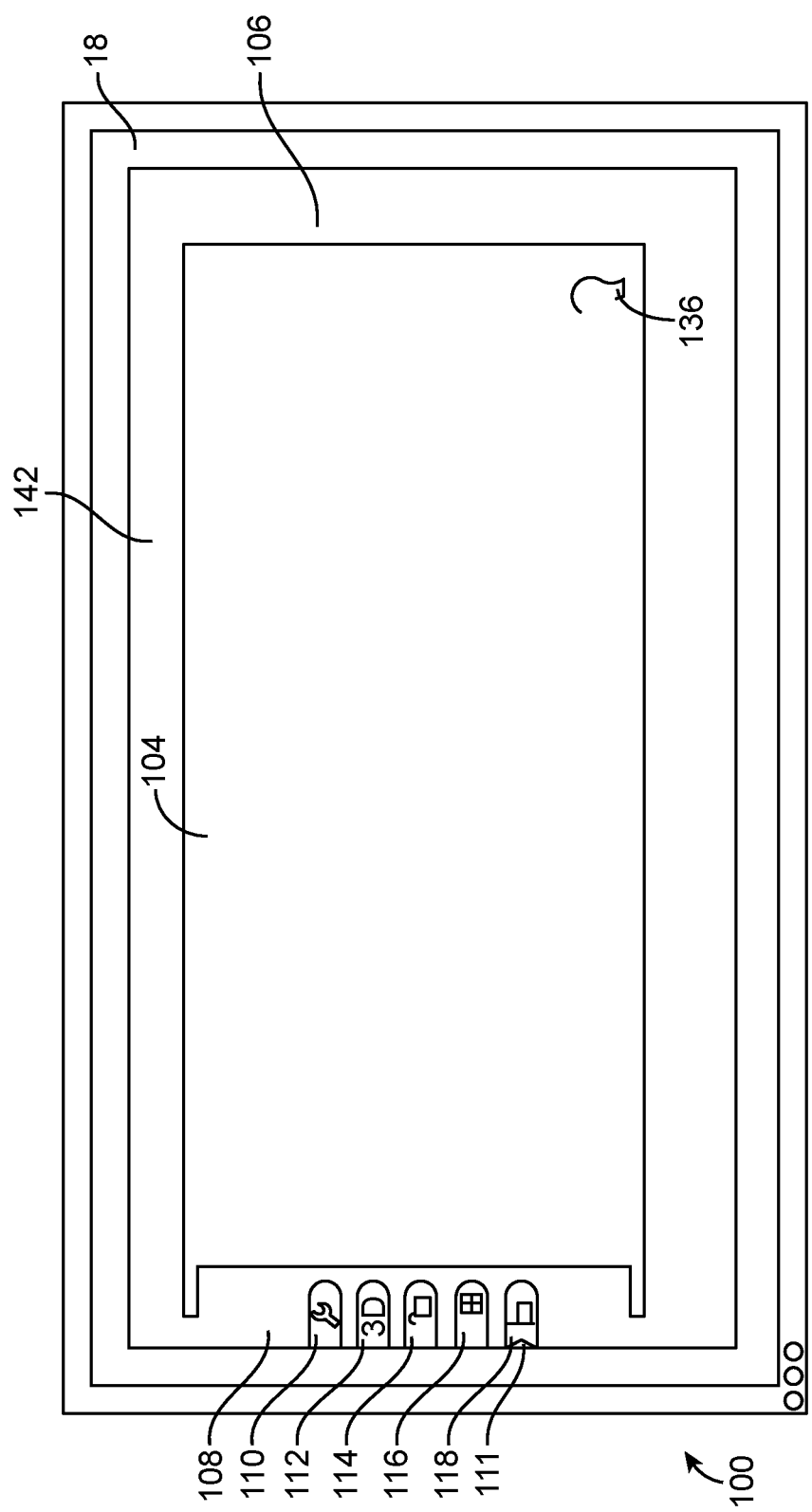
FIG. 17 shows the graphical user interface in which the ultrasound data has been made full screen and the navigational screen has been eliminated.

Selecting control 118 (FIG. 16) with navigational tool 111 causes the system to exit the display of FIG. 3 and go to the display of FIG. 17. FIG. 17 illustrates a full screen view of the ultrasound data of screen 104, eliminating everything else from the display except for overlay 142, which contains control tab 108 with controls 110, 112, 114, 116, and 118. Overlay 142 is substantially similar to overlay 102 in appearance except without the division into two screens.

It will be appreciated by those skilled in the art that changes can be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A system for guiding a surgeon to position a medical device in a patient, comprising:
    an ultrasound device configured to acquire an ultrasound image of an area within the patient; and
    a processing unit configured to communicatively couple with the ultrasound device, wherein the processing unit is configured to communicatively couple to a display device, wherein the processing unit is configured to output to the display device a graphical user interface including an avatar of the ultrasound device and an avatar of an ultrasound imaging plane, wherein the avatar of the ultrasound device and the avatar of the ultrasound imaging plane correspond with the ultrasound image;
    wherein the graphical user interface includes a graphical object separate from the ultrasound image, the graphical object being different from the avatar of the ultrasound device and from the avatar of the ultrasound imaging plane, and wherein the graphical object is configured to indicate a position of the ultrasound device from a point of view of the surgeon with respect to an anatomical part of the patient.

2. The system of claim 1, wherein the graphical object comprises a head icon.

3. The system of claim 2, wherein the head icon is spaced apart from the avatar of the ultrasound imaging plane.

4. The system of claim 1, wherein the avatar of the ultrasound device and the avatar of the ultrasound imaging plane together indicate an imaging direction of the ultrasound device.

5. The system of claim 1, wherein the ultrasound device is configured to image the area in a torso of the patient.

6. The system of claim 1, wherein the avatar of the ultrasound imaging plane extends from the avatar of the ultrasound device.

7. The system of claim 1, wherein the graphical user interface includes a representation of the medical device having a positional relationship with respect to the avatar of the ultrasound imaging plane.

8. The system of claim 7, wherein the representation of the medical device comprises a representation of an ablation device.

9. The system of claim 1, wherein the graphical user interface includes a meter indicating a distance measured from a tip of the medical device.

10. The system of claim 9, wherein the distance is from the tip of the medical device to the ultrasound imaging plane.

11. The system of claim 9, wherein the meter is color coded.

12. The system of claim 11, wherein the meter comprises a first mark having a first color for indicating that the medical device is in front of the ultrasound imaging plane.

13. The system of claim 12, wherein the meter comprises a second mark having a second color that is different from the first color, wherein the second mark having the second color is configured to indicate that the medical device is behind the ultrasound imaging plane.

14. The system of claim 1, wherein the graphical user interface has a split-screen configuration with a first display area and a second display area.

15. The system of claim 14, wherein the graphical user interface includes a proximity meter between the first display area and the second display area.

16. A method for guiding a surgeon to position a medical device in a patient, comprising:
    acquiring, by an ultrasound device, an ultrasound image of an area within the patient; and
    outputting, by a processing unit, to a display device, a graphical user interface including an avatar of the ultrasound device and an avatar of an ultrasound imaging plane, wherein the avatar of the ultrasound device and the avatar of the ultrasound imaging plane correspond with the ultrasound image; and
    wherein the graphical user interface includes a graphical object separate from the ultrasound image, the graphical object being different from the avatar of the ultrasound device and from the avatar of the ultrasound imaging plane, and wherein the graphical object is configured to indicate a position of the ultrasound device from a point of view of the surgeon with respect to an anatomical part of the patient.

17. The method of claim 16, wherein the graphical object comprises a head icon.

18. The method of claim 16, wherein the graphical user interface includes a representation of the medical device having a positional relationship with respect to the avatar of the ultrasound imaging plane.

19. The method of claim 16, wherein the graphical user interface includes a meter indicating a distance measured from a tip of the medical device.

20. The method of claim 19, wherein the meter comprises a first mark having a first color, and a second mark having a second color that is different from the first color;
wherein the first mark having the first color is configured to indicate that the medical device is in front of the ultrasound imaging plane; and
wherein the second mark having the second color is configured to indicate that the medical device is behind the ultrasound imaging plane.

* * * * *